US00PP30971P2

(12) United States Plant Patent
Ubink

(10) Patent No.: US PP30,971 P2
(45) Date of Patent: Oct. 22, 2019

(54) ***PACHYPHYTUM* PLANT NAMED 'UB-PACHY-1801'**

(50) Latin Name: *Pachyphytum bracteosum*
Varietal Denomination: UB-PACHY-1801

(71) Applicant: Gert Ubink, Kudelstaart (NL)

(72) Inventor: Gert Ubink, Kudelstaart (NL)

(73) Assignee: Handelskwekerijubink BV (NL)

( * ) Notice: Subject to any disclaimer, the term of this patent is extended or adjusted under 35 U.S.C. 154(b) by 0 days.

(21) Appl. No.: 16/350,239

(22) Filed: Oct. 16, 2018

(51) Int. Cl.
*A01H 5/00* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Pachyphytum* cultivar named 'UB-PACHY-1801' is disclosed, characterized by foliage which is strong and strongly held on the plant, resisting both dropping and breaking off. Foliage has a distinct upward curve, giving the appearance of a full-bodied plant. Foliage is distinctly more lancet-like in shape. The new variety is a *Pachyphytum*, useful as both an indoor ornamental plant, as well as an outdoor garden or container plant.

2 Drawing Sheets

Latin name of the genus and species: *Pachyphytum bracteosum.*

Variety denomination: 'UB-PACHY-1801'.

BACKGROUND OF THE INVENTION

The new cultivar, *Pachyphytum* 'UB-PACHY-1801', is the product of a planned breeding program. The new variety originated from a cross pollination of the seed parent, an unnamed, unpatented *Pachyphytum bracteosum* with the pollen parent an unnamed, unpatented, *Pachyphytum hookeri*. The cross pollination was made during Spring of 2012 in Kudelstaart, the Netherlands, at a commercial greenhouse. The new cultivar 'UB-PACHY-1801' was first selected by the inventor, Gert Ubink, during 2013.

Asexual reproduction of the new cultivar 'UB-PACHY-1801' was first performed in Kudelstaart, the Netherlands, by terminal vegetative cuttings in 2013. *Pachyphytum* 'UB-PACHY-1801' has since produced at least 3 generations and has shown that the unique features of this cultivar are stable and reproduced true to type. 'UB-PACHY-1801' was first made available to the public Apr. 1, 2018, in the Netherlands. This sale was made directly by the inventor or one who obtained the claimed invention directly or indirectly from the inventor. This sale and all public disclosures made between Apr. 1, 2018 and the filing of this application fall within the exception allowed under 102(b)(1).

SUMMARY OF THE INVENTION

The cultivar 'UB-PACHY-1801' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UB-PACHY-1801'. These characteristics in combination distinguish 'UB-PACHY-1801' as a new and distinct *Pachyphytum* cultivar:

1. Leaves are strong and strongly held, resistant to both dropping and breaking off.
2. Leaves curve upwards, giving plant more body.
3. More lancet-like shaped leaves.

PARENTAL COMPARISON

Plants of the new cultivar 'UB-PACHY-1801' are similar to plants of the seed parent in most horticultural characteristics. However, plants of the new cultivar 'UB-PACHY-1801' differ in the following:

1. Leaves of new variety are much more firmly fixed to plant stem than leaves of the seed parent.
2. Plants of the new cultivar are wider than plants of the seed parent.
3. New variety has shorter internodes than the seed parent.

Plants of the new cultivar 'UB-PACHY-1801' are similar to the pollen parent in most horticultural characteristics. However, plants of the new cultivar 'UB-PACHY-1801' differ in the following:

1. The new variety's leaves are wider than leaves of the pollen parent.
2. The new variety's leaves are much more flat than leaves of pollen parent.

COMMERCIAL COMPARISON

The new cultivar 'UB-PACHY-1801' can be compared to the unpatented commercial variety *Pachyphytum* 'DRACO'. Plants of the new cultivar 'UB-PACHY-1801' are similar to 'DRACO' in most horticultural characteristics. However, plants of the new cultivar 'UB-PACHY-1801' differ in the following:

1. 'UB-PACHY-1801' has a blue-green leaf color; 'DRACO' has a slightly purple leaf color.
2. 'UB-PACHY-1801' has more lancet-shaped leaves than 'DRACO'.

The new cultivar 'UB-PACHY-1801' can be compared to the unpatented commercial variety *Pachyphytum* 'Lila Cina'. Plants of the new cultivar 'UB-PACHY-1801' are similar to 'Lila Cina' in most horticultural characteristics. However, plants of the new cultivar 'UB-PACHY-1801' differ in the following:

1. 'UB-PACHY-1801' has a blue-green leaf color; 'Lila Cina' has a grey leaf color.
2. 'UB-PACHY-1801' has more lancet-shaped leaves than 'Lila Cina'.
3. 'UB-PACHY-1801' has more upright-growing leaves; 'Lila Cina' has more flat leaves.

BRIEF DESCRIPTION OF THE PHOTOGRAPHS

The accompanying photographs in FIG. 1 and FIG. 2 illustrate in full color typical plants of 'UB-PACHY-1801' grown in a greenhouse in Kudelstaart, The Netherlands. The photographs were taken using conventional techniques and equipment. The plant photographed is 12 months old. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Pachyphytum* plant. The following photographs depict plants grown under two different natural light conditions. Temperatures ranged from approximately 2° C. to 38° C. night and day. No artificial light, photoperiodic treatments or chemical treatments were given to the plants.

DETAILED BOTANICAL DESCRIPTION

Figure 1:
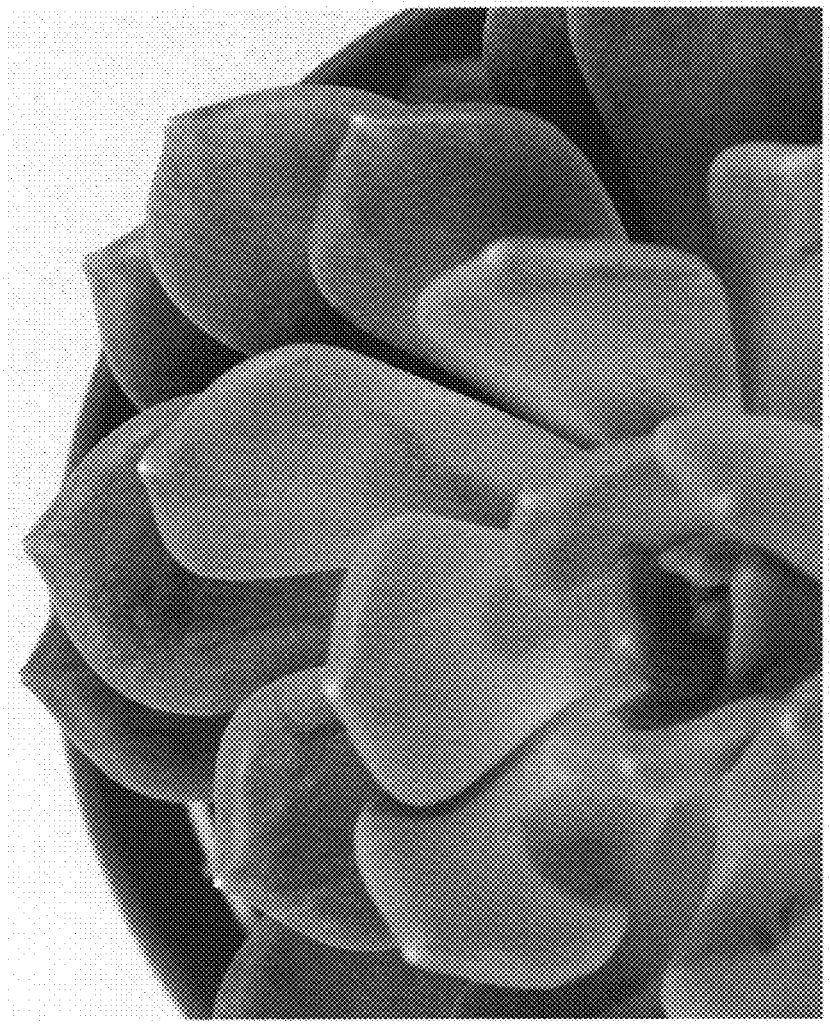
FIG. 1 illustrates in full color a top view of a typical of plant of *Pachyphytum* 'UB-PACHY-1801' grown in a greenhouse in Kudelstaart, The Netherlands, under moderate light conditions of approximately 2500 to 3500 foot candles. This figure highlights the foliar rosette.
Figure 2:
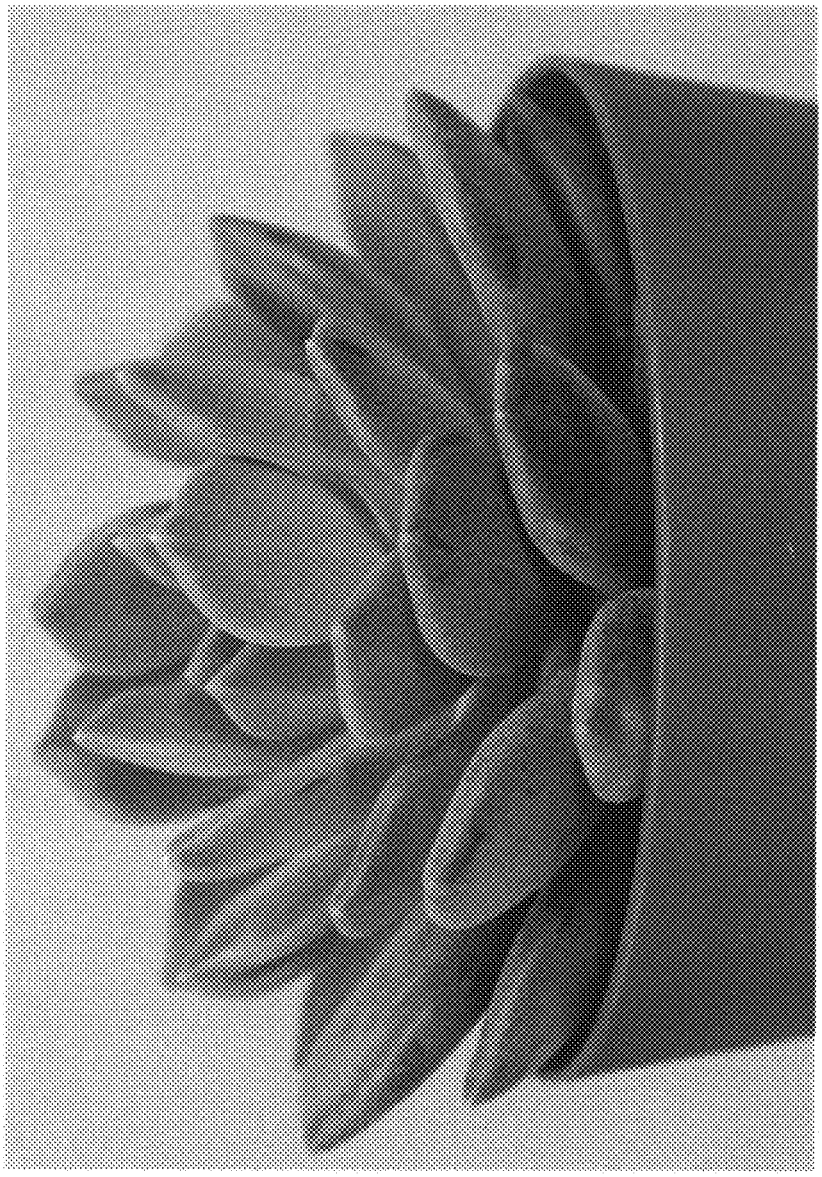
FIG. 2 illustrates in full color a side view of a typical of plant of *Pachyphytum* 'UB-PACHY-1801'. This figure highlights the leaf angle of attachment.

In the following description, color references are made to The Royal Horticultural Society Colour Chart, 2007, except where general terms of ordinary dictionary significance are used. The following observations and measurements describe 'UB-PACHY-1801' plants in a commercial greenhouse in Aalsmeer, the Netherlands. Temperatures ranged from about 14° C. to 16° C. at night and about 18° C. to 20° C. during the day. No artificial light, photoperiodic treatments or chemical treatments were given to the plants. Measurements and numerical values represent averages of typical plant types.

Botanical classification: *Pachyphytum* 'UB-PACHY-1801'.

PROPAGATION

Type of propagation typically used: Terminal vegetative cuttings, from side shoots.

Time to initiate roots: About 14 days at approximately 20° C.

Root description: Fibrous, fine, dense, freely branching. White to tan, not accurately measured with an R.H.S. chart.

Crop time: Approximately 52 weeks from propagation to saleable plant.

PLANT

Age of plant described: 12 months from a cutting.

Container size of the plant described: 10.5 cm.

Growth habit: Basal rosette.

Height: Approximately 7.9 cm.

Plant spread: Approximately 12.2 cm.

Growth rate: Leaves grow approximately 0.5 cm per month.

Branching characteristics: Basal rosette. No branching, no stems or lateral branches.

FOLIAGE

Leaf:

*Arrangement.*—Rosette.

*Average length.*—5.9 cm.

*Average width.*—2.4 cm.

*Thickness of leaf.*—Thickest section, near center of leaf 1.1 cm, on average.

*Shape of blade.*—Oblanceolate, succulent, slightly to moderately concave, very slightly carinate.

*Apex.*—Broad short apiculate to abruptly acute.

*Base.*—Broad cuneate.

*Margin.*—Entire.

*Texture of top surface.*—Glabrous. Glaucous.

*Texture of bottom surface.*—Glabrous. Glaucous.

*Appearance of top surface.*—Matte.

*Appearance of bottom surface.*—Matte.

*Quantity of leaves per rosette.*—Average 41.

*Color.*—Young foliage upper side: RHS Greyed-Green 191A; base Yellow-Green 145D; whole leaf covered with waxy layer of Greyed-Green 188A to 188B. Young foliage, under side: RHS Greyed-green 191A; base Yellow-Green 145D; whole leaf covered with waxy layer of Greyed-Green 188A. Mature foliage upper side: Slightly darker than RHS Greyed-Green 191A; base Yellow-Green 145D; whole leaf covered with waxy layer of Greyed-Green 188A to 189B. Mature foliage, under side: RHS Greyed-Green 191A; base Yellow-Green 145D; whole leaf covered with waxy layer of Greyed-Green 188A to 189B.

*Venation.*—There is no visual appearance of venation.

FLOWER

No flowers observed to date.

REPRODUCTIVE ORGANS

No flowers observed to date.

OTHER CHARACTERISTICS

Fruits and seeds: None observed to date.

Temperature tolerance: Low temperature to approximately 10° C. High temperature to approximately 40° C.

Disease/pest resistance: Neither resistance nor susceptibility to normal diseases and pests typical to Genus have been observed.

Drought tolerance: As a succulent plant, 2 to 3 weeks of drought tolerance can be expected.

What is claimed is:

1. A new and distinct cultivar of *Pachyphytum* plant named 'UB-PACHY-1801' as herein illustrated and described.

* * * * *